United States Patent [19]

Harada et al.

[11] Patent Number: 5,242,451
[45] Date of Patent: Sep. 7, 1993

[54] INSTRUMENT FOR RETAINING INNER DIAMETER OF TUBULAR ORGAN LUMEN

[75] Inventors: Fumiaki Harada; Toshinobu Ishida, both of Fuji, Japan

[73] Assignee: Terumo Kabushiki Kaisha, Tokyo, Japan

[21] Appl. No.: 924,378

[22] Filed: Jul. 31, 1992

Related U.S. Application Data

[63] Continuation of Ser. No. 829,607, Jan. 29, 1992, abandoned, which is a continuation of Ser. No. 474,769, Mar. 19, 1990, filed as PCT/JP88/00960, Sep. 9, 1988, publish as WO89/02755, Apr. 6, 1989, abandoned.

[30] Foreign Application Priority Data

Sep. 24, 1987 [JP] Japan .................. 62-237510

[51] Int. Cl.$^5$ .............................. A61F 11/00
[52] U.S. Cl. .................. 606/108; 606/198; 623/1; 623/12
[58] Field of Search ............ 606/191, 194, 195, 198, 606/108, 200; 604/96, 105, 104; 623/1, 12

[56] References Cited

U.S. PATENT DOCUMENTS

| | | |
|---|---|---|
| 3,868,956 | 3/1975 | Alfidi et al. . |
| 4,503,569 | 3/1985 | Dotter . |
| 4,512,338 | 4/1985 | Balko et al. . |
| 4,553,545 | 11/1985 | Maass et al. . |
| 4,665,918 | 5/1987 | Garza et al. . |
| 4,681,110 | 7/1987 | Wiktor . |
| 4,795,458 | 1/1989 | Regan ............ 623/1 |
| 4,954,126 | 9/1990 | Wallstén ........ 623/1 |

FOREIGN PATENT DOCUMENTS

| | | |
|---|---|---|
| 0119688A-3 | 9/1984 | European Pat. Off. . |
| 57-89859 | 6/1982 | Japan . |
| 58-176154 | 4/1983 | Japan . |
| 58-501458 | 9/1983 | Japan . |
| 60-220030 | 11/1985 | Japan . |
| 61-6655 | 2/1986 | Japan . |
| 61-220648 | 9/1986 | Japan . |
| 62-82975 | 4/1987 | Japan . |
| 62-82976 | 4/1987 | Japan . |
| WO83/00997 | 3/1983 | World Int. Prop. O. . |

Primary Examiner—John D. Yasko
Assistant Examiner—William Lewis
Attorney, Agent, or Firm—Frishauf, Holtz, Goodman & Woodward

[57] ABSTRACT

An inner diameter retaining instrument for holding a predetermined expansion state of the lumen of a tubular organ such as a blood vessel, a digestive tract, or a windpipe is disclosed. This instrument is formed into a cylindrical shape or substantially cylindrical shape by a unidirectional shape memory alloy. The outer diameter of the cylindrical body at its transformation temperature (e.g., a temperature higher than a body temperature) is set to be smaller than the inner diameter of a tubular organ in which the cylindrical body is introduced. The instrument can be deformed to be radially expanded at, e.g., the body temperature or lower. As a cylindrical shape, a coil-like shape, a shape having a spiral section, a shape having a slit in its longitudinal direction, or a mesh-like shape can be arbitrarily selected.

14 Claims, 4 Drawing Sheets

F I G. 1A        F I G. 1B
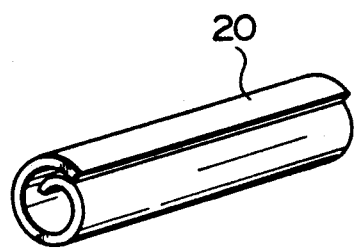
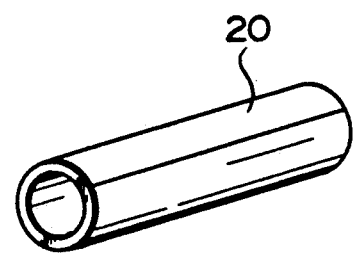
F I G. 2A        F I G. 2B

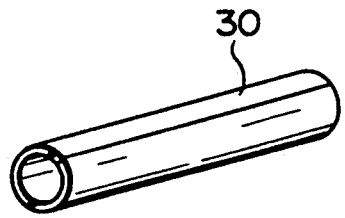
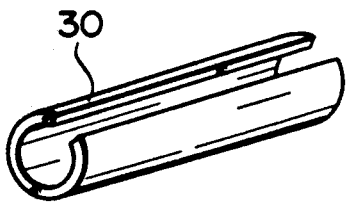
FIG. 3A                FIG. 3B
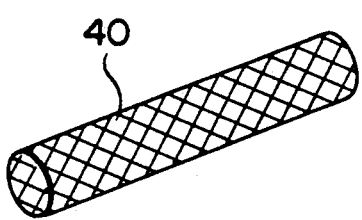
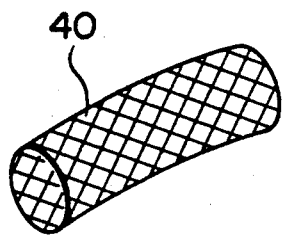
FIG. 4A                FIG. 4B

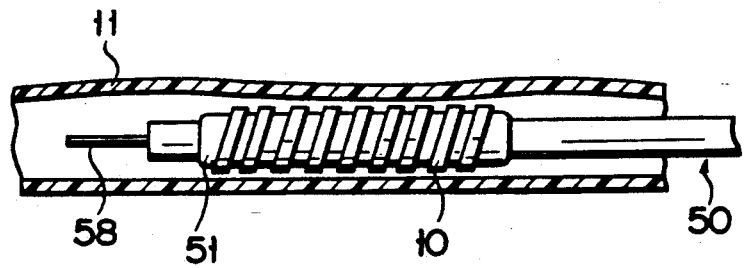
F I G. 5A
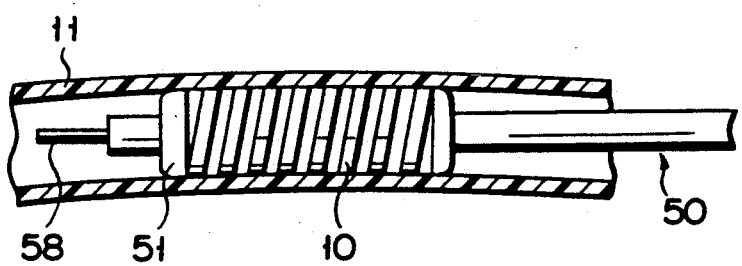
F I G. 5B
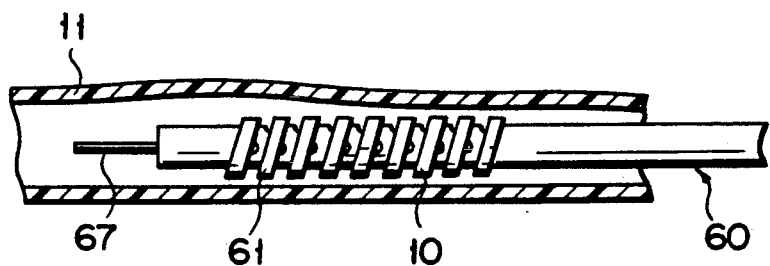
F I G. 5C

INSTRUMENT FOR RETAINING INNER DIAMETER OF TUBULAR ORGAN LUMEN

This application is a continuation of application Ser. No. 07/829,607, filed Jan. 29, 1992, abandoned, which is a continuation of Ser. No. 07/474,769, filed Mar. 19, 1990, filed as PCT/JP88/00960, Sep. 9, 1988, publish as WO89/02755, Apr. 6, 1989 (now abandoned).

TECHNICAL FIELD

The present invention relates to an inner diameter retaining instrument for keeping a desired inner diameter of a tubular organ lumen such as a blood vessel, a digestive tract, or a windpipe.

BACKGROUND ART

After a constricted portion of, e.g., a coronary artery is expanded by a blood vessel expanding catheter, in order to prevent reconstriction of the expanded portion, an inner diameter retaining instrument (stent) for ensuring the inner diameter of the lumen of a tubular organ has been proposed.

A conventional inner diameter retaining instrument disclosed in Japanese Patent Publication (Kokoku) No. 61-6655 employs a unidirectional shape memory alloy. This alloy is formed into a tubular shape having an inner diameter substantially equal to an inner diameter of a normal blood vessel to memorize the shape. The alloy is then deformed to reduce its outer diameter so as to be easily inserted in the blood vessel. The resultant structure is then introduced to a desired position in the blood vessel. Thereafter, the structure is heated by warm water and is restored to the memorized shape.

The above conventional inner diameter retaining instrument consisting of a unidirectional shape memory alloy, however, cannot be deformed unless an external force is applied thereto once the instrument is restored to its memorized shape and is expanded. For this reason, even if an affected portion is restored after indwelling of the inner diameter retaining instrument, the instrument cannot be removed, thus posing a serious problem in terms of adaptability with a living body. In addition, even if it is found upon expansion of the inner diameter retaining instrument that the instrument is indwelled at a wrong position, it is very difficult to change the indwelling position.

It is an object of the present invention to provide an instrument for retaining the inner diameter of a tubular organ lumen, which can be caused to freely contract even after it is expanded in a tubular organ, thereby enabling recovery from an indwelling position and arbitrary change in indwelling position upon expansion.

SUMMARY OF INVENTION

According to the normal present invention, therefore, there is provided an instrument for retaining the inner diameter of a tubular organ lumen characterized in that the instrument is formed into a substantially cylindrical body by a unidirectional shape memory alloy so as to be radially changed in size with changes in temperature, and the outer diameter of the cylindrical body in its basic phase is set to be smaller than the inner diameter of a tubular organ in which the cylindrical body is introduced.

Note that the diameter of the cylindrical body is preferably changed to the diameter of the basic phase at a temperature higher than a body temperature, and it is preferable that the body can be deformed to a radially expanded state by an external force at a body temperature or lower. As a shape of the cylindrical body, a coil-like shape, a shape having a spiral section, a shape having a slit in its longitudinal direction, a mesh-like shape, a fabric-like shape, and the like can be properly selected. As a unidirectional shape memory alloy, a Ti-Ni alloy, a Cu-Al-Ni alloy, a Cu-Zn-Al alloy, or the like can be used.

According to the present invention, a cylindrical body as an inner diameter retaining instrument is deformed to have a diameter smaller than the inner diameter of a tubular organ at a transformation temperature of a shape memory alloy constituting the cylindrical inner diameter retaining instrument or lower. The cylindrical body is then fitted on an end balloon or the like of, e.g., a tubular organ expanding catheter, and is introduced to a desired position in the tubular organ. Thereafter, the diameter of the cylindrical body is increased by the effect of an external mechanical force due to the expansion of the balloon or the like, thus retaining the inner diameter of the tubular organ. The balloon is then caused to contract to extract the catheter. Hence, the cylindrical body can be indwelled in the tubular organ.

When the indwelled inner diameter retaining instrument is to be recovered, or the indwelling position is to be changed, a catheter having a side hole formed in, e.g., its distal end portion is introduced to the indwelling position of the cylindrical body, and a solution of a temperature exceeding the transformation temperature of the memory shape alloy is supplied from the side hole. As a result, the temperature of the cylindrical body exceeds the transformation temperature, and the cylindrical body is restored to the memorized shape, i.e., reduced in diameter to be smaller than the inner diameter of the tubular organ. Thus, the cylindrical body can be moved by moving the catheter while the cylindrical body is fitted on, e.g., the distal end portion of the catheter. That is, according to the present invention, even if the instrument is expanded once in a tubular organ, it can be freely reduced in size. Therefore, recovery of the instrument from an indwelling position can be performed, and the indwelling position can be freely changed upon expansion of the instrument.

In the present invention, a unidirectional shape memory alloy means an alloy which causes thermoelastic martensite transformation and is deformed into a memorized shape in the basic phase at a reverse transformation temperature or higher. This alloy can be freely deformed at the transformation temperature or lower. After the temperature becomes the transformation temperature or higher and the alloy is restored to the memorized shape, the alloy maintains its memorized shape even if the temperature becomes the transformation temperature or lower unless an external force is applied.

In addition, as a shape memory alloy constituting the inner diameter retaining instrument of the present invention, a Ti-Ni alloy (composition: about 50 at% Ni, transformation temperature: 45° C.) is, for example, suitably used.

BRIEF DESCRIPTION OF THE DRAWINGS

FIGS. 1(A) and 1(B) are side views showing an inner diameter retaining instrument according to a first embodiment of the present invention;

FIGS. 2(A) and 2(B) are perspective views showing an inner diameter retaining instrument according to a second embodiment of the present invention;

FIGS. 3(A) and 3(B) are perspective vies showing an inner diameter retaining instrument according to a third embodiment of the present invention;

FIGS. 4(A) and 4(B) are perspective views showing an inner diameter retaining instrument according to a fourth embodiment of the present invention;

FIGS. 5(A) and 5(B) are views each illustrating an indwelling state of the inner diameter retaining instrument;

FIG. 5(C) is a view illustrating a recovery state of the inner diameter retaining instrument;

DESCRIPTION

Figure 6:
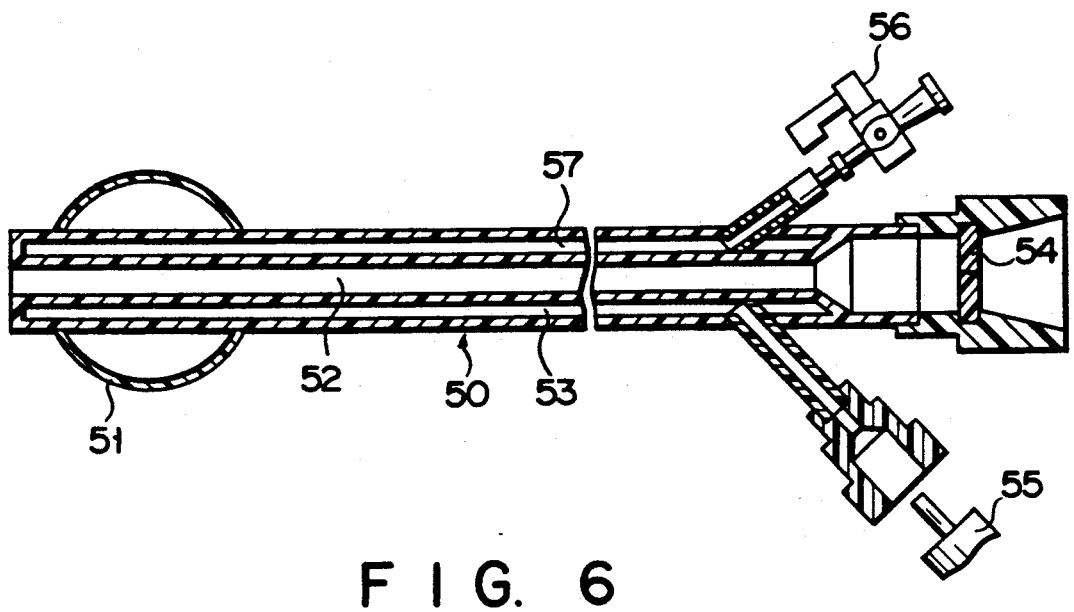
FIG. 6 is a sectional view showing indwelling catheter.

Embodiments of the present invention will be described below with reference to the accompanying drawings.

An inner diameter retaining instrument (to be referred to as a stent hereinafter) 10 shown in FIGS. 1(A) and 1(B) is formed into a substantially cylindrical shape and is made of a unidirectional shape memory alloy. In this case, the stent 10 has a coil-like shape. The diameter of the stent 10 in its basic phase is set to be smaller (see FIG. 1(A)) than the inner diameter of a tubular organ, i.e., a blood vessel 11 in this case (see FIG. 5(A)). Furthermore, in this case, the transformation temperature of the shape memory alloy constituting the stent 10 is set to be higher than a body temperature so that the stent 10 is reduced in size in its radial direction at a temperature exceeding the body temperature. The stent 10 can be radially expanded by an external force (see FIG. 1(B)).

In addition to the coil-like stent 10 according to the first embodiment, a stent of the present invention broadly includes substantially cylindrical stents. In this case, a substantially cylindrical stent includes stents having outer surfaces which can expand a tubular organ lumen during expansion thereof and can maintain its expansion state.

More specifically, a stent 20 according to a second embodiment is constituted by a stent having a spiral section, which is changed from a contracted state shown in FIG. 2(A) to an expanded state shown in FIG. 2(B).

A stent 30 according to a third embodiment is constituted by a tubular stent having a slit formed in its longitudinal direction, which is changed from a contracted state shown in FIG. 3(A) to an expanded state shown in FIG. 3(B).

A stent 40 according to a fourth embodiment is constituted by a mesh-like stent which is changed from a contracted state shown in FIG. 4(A) to an expanded state shown in FIG. 4(B). End portions of the mesh-like stent are preferably welded or fixed by an adhesive to prevent shape memory alloy thin wires from becoming loose.

In order to indwell the stent of the present invention at a desired position in a tubular organ, an indwelling catheter 50 shown in, e.g., FIG. 6 is used. The indwelling catheter 50 comprises a balloon 51 at its distal end portion. The balloon 51 communicates with a sub-path 53 for liquid injection of the catheter 50 through a side hole 57. The catheter 50 has a main path 52 at its central portion. A guide wire 58 can be inserted in the main path 52 (see FIGS. 5(A) and 5(B)). Therefore, the catheter 50 can be introduced to a desired portion of a tubular organ by inserting the guide wire 58, which has been inserted to the desired portion of the tubular organ in advance, into the main path. A balloon expanding solution is then injected in the sub-path 53 of the catheter 50 to expand the balloon 51. As a result, an external expanding force is mechanical applied to a contracted stent 10 (see FIG. 5(A)) which has been fitted on the outer surface of the balloon 51, and the stent 10 is expanded to be brought into contact with the inner wall of a tubular organ 11, as shown in FIG. 5(B).

A check valve 54 is arranged on a hub of the main path 52 so as to allow the guide wire to pass therethrough and prevent leakage of blood or the like. Reference numeral 55 denotes a liquid injection device; and 57, an exhausting sub-path communicating with the inner space of the balloon 51. A three-way plug 56 or the like is arranged at the proximal end portion of the path 57.

Figure 7:
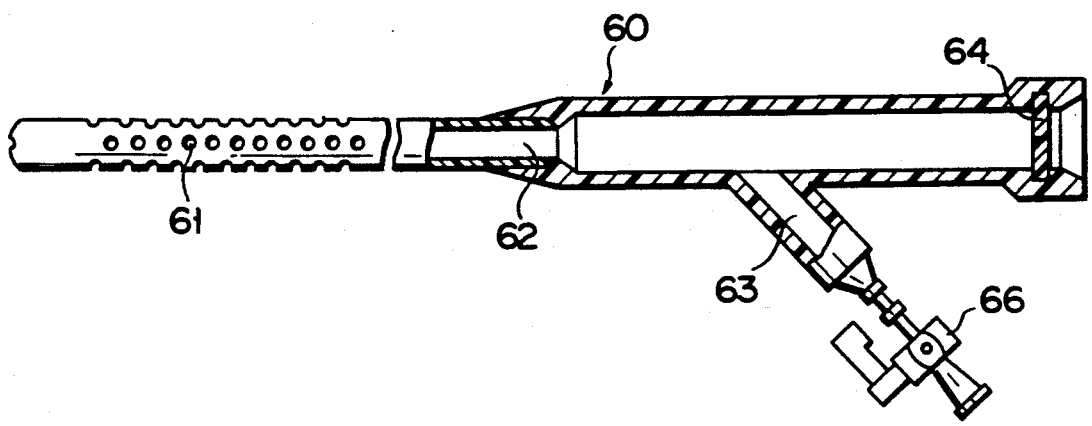
FIG. 7 is a sectional view showing a recovery catheter.

In order to recover (or change an indwelling position of) the stent of the present invention after indwelling thereof, a recovery catheter 60, for example, shown in FIG. 7 is used. The recovery catheter 60 comprises a side hole 61 communicating with a main path 62 at its distal end portion. The catheter 60 is guided to a stent indwelling portion in a tubular organ by a guide wire (denoted by reference numeral 67 in FIG. 5(C)) inserted in the main path 62. A stent heating liquid is then supplied into the main path 62 through a sub-path 63 for liquid injection. The liquid is flowed out from the side hole 61 to heat the expanded stent located around the side hole 61 to the transformation temperature or higher so as to restore the memorized shape in the basic phase, i.e., be reduced in size. A check valve 64 is arranged on a hub of the main path 62 so as to allow the guide wire to pass therethrough and prevent the leakage of blood or the like. A three-way plug 66 for injecting a stent heating liquid is arranged on a hub of the sub-path 63.

Functions of the above-described stent 1 will be described below.

According to the stent 10, the stent 10 is deformed to have a diameter smaller than the inner diameter of the blood vessel 11 at the transformation temperature of the shape memory alloy or lower. The stent 10 is then fitted on the balloon 51 attached to the distal end portion of the indwelling catheter 50, and the resultant structure is introduced to a desired position of the blood vessel 11, as shown in FIG. 5(A). Thereafter, the stent 10 is expanded by the effect of an external force derived from the expansion of the balloon 51 and is indwelled in the blood vessel 11, thus retaining the inner diameter thereof, as shown in FIG. 5(B).

When the above stent 10 is to be recovered, or its indwelling position is to be changed, a recovery catheter 60 having a side hole 61 at its distal end is introduced into the indwelling position of the stent 10, as shown in FIG. 5(C). Thereafter, a liquid at the transformation temperature of the stent 10 or higher is supplied through the side hole 61 so as to increase the temperature of the stent 10 to the transformation temperature or higher, thereby restoring the memorized shape, i.e., reducing the diameter of the stent 10 to be smaller than the inner diameter of the blood vessel 11. As a result, the stent 10 can be moved upon movement of the catheter 60 while the stent 10 is wound around the distal end of the catheter 60.

That is, according to the above-described stent 10, even if the stent 10 is expanded in the blood vessel 11 once, it can be freely contracted again. Therefore, recovery of the stent 10 from its indwelling position can be performed, and the indwelling position after expansion of the stent 10 can be freely changed.

An example of the present invention will be described below.

A mesh-like cylindrical body or member having an outer diameter of 1.5 mm was made of an Ni-Ti shape memory alloy wire having a diameter of 0.1 mm. The Ni-Ti shape memory alloy wire had a composition allowing restoration of a memorized shape at a temperature near 45° C. after it was deformed upon application of an external force. When this cylindrical body or member was attached to a balloon having an expansion diameter of 3.0 mm of a PTCA expanding catheter and the balloon was expanded, the cylindrical body could be indwelled in the lumen of a silicone tube having an inner diameter of 2.55 mm. Thereafter, a catheter (outer diameter: 1.8 mm) having a side hole at its distal end portion was inserted in the cylindrical body to position the side hole at the indwelling position of the cylindrical body. When warm water at 45° C. was then flowed out from the side hole, the cylindrical body was wound around the distal end portion of the catheter, and could be recovered. Industrial Applicability The inner diameter retaining instrument of the present invention can be effectively used to expand a constricted portion of a tubular organ lumen such as a blood vessel, a digestive tract, or a windpipe and to ensure its inner diameter.

We claim:

1. A system for maintaining an inner diameter of a tubular organ lumen of a living body, which system comprises:
   (a) an inner diameter retaining instrument comprising:
      a cylindrical member made of a unidirectional shape memory alloy whose transformation temperature is higher than a body temperature of a living body in which the cylindrical member is to placed,
      said cylindrical member being radially expandable by an external force at a body temperature of the living body, and
      an outer diameter of said cylindrical member in a basic phase thereof when heated to said transformation temperature being set to be smaller than an inner diameter of a tubular body organ of the living body in which said cylindrical member is to be introduced; and
   (b) a recovery catheter comprising a main tubular body having a plurality of side holes provided at a distal end portion thereof and a heating liquid supply port provided at a proximal end thereof for introducing a heated liquid into the main tubular body for heating said inner diameter retaining instrument through said side holes to constrict said inner diameter retaining instrument to said basic phase so as to mount said inner diameter retaining instrument on said distal end portion of said recovery catheter.

2. A system according to claim 1, wherein said cylindrical member comprises a coil-like body.

3. A system according to claim 1, wherein said cylindrical body comprises a member having a spiral section.

4. A system according to claim 1, wherein said cylindrical body comprises a tubular member having slit in a longitudinal direction thereof.

5. A system according to claim 1, wherein said cylindrical body comprises a mesh-like member.

6. A system according to claim 1, wherein said cylindrical member comprises a fabric made of a shape memory alloy thin wire.

7. A system according to claim 1, wherein said unidirectional shape memory alloy is an alloy selected from the group consisting of Ti-Ni, Cu-Al-Ni, and Cu-Zn-Al alloys.

8. A system for maintaining an inner diameter of a tubular organ lumen of a living body, which system comprises:
   (a) an indwelling balloon catheter having:
      means defining a main path formed along and coaxially with said indwelling balloon catheter for inserting a guide wire therein,
      means defining a sub-path formed along said main path for passing a balloon expanding liquid therethrough, and
      a balloon mounted in a contracted state at a distal end portion of said indwelling balloon catheter in communication with said sub-path so a to receive said balloon expanding liquid and to be expandable by said balloon expanding liquid; and
   (b) an inner diameter retaining instrument comprising:
      cylindrical member made of a unidirectional shape memory alloy whose transformation temperature is higher than a body temperature of a living body in which the cylindrical member is to be placed,
      said cylindrical member being fitted on said balloon with said balloon in said contracted state and said cylindrical member being radially expandable at a body temperature of the living body by an expansion of said balloon, and
      an outer diameter of said cylindrical member in a basic phase thereof when heated to said transformation temperature being set to be smaller than an inner diameter of a tubular body organ of the living body in which said cylindrical member is to be introduced.

9. A system according to claim 8, wherein said cylindrical member comprises a coil-like body.

10. A system according to claim 8, wherein said cylindrical member comprises a body having a spiral section.

11. A system according to claim 8, wherein said cylindrical member comprises a tubular body having slit in a longitudinal direction thereof.

12. A system according to claim 8, wherein said cylindrical member comprises a mesh-like body.

13. A system according to claim 8, wherein said cylindrical member comprises a fabric made of a shape memory alloy thin wire.

14. A system according to claim 8, wherein said unidirectional shape memory is an alloy selected from the group consisting of Ti-Ni and Cu-Al alloys.

* * * * *